United States Patent
Yu et al.

(10) Patent No.: US 9,810,662 B1
(45) Date of Patent: Nov. 7, 2017

(54) STRUCTURE FOR INTEGRATING MICROFLUIDIC DEVICES AND ELECTRICAL BIOSENSORS

(71) Applicants: CHIP WIN TECHNOLOGY CO., LTD., Hsinchu County (TW); Chao-Ching Yu, Taoyuan (TW)

(72) Inventors: Chao-Ching Yu, Taoyuan (TW); Lin-Ta Chung, Hsinchu County (TW); Hsi-Ying Yuan, Hsinchu County (TW); Ke-Pan Liao, Hsinchu County (TW)

(73) Assignees: CHIP WIN TECHNOLOGY CO., LTD., Hsinchu (TW); Chao-Ching Yu, Taoyuan (TW)

( * ) Notice: Subject to any disclaimer, the term of this patent is extended or adjusted under 35 U.S.C. 154(b) by 0 days.

(21) Appl. No.: 15/406,809

(22) Filed: Jan. 16, 2017

(30) Foreign Application Priority Data

Aug. 19, 2016 (TW) .............................. 105126570 A

(51) Int. Cl.
*G01N 27/414* (2006.01)
*H01L 21/76* (2006.01)
*H01L 29/772* (2006.01)
*H01L 29/00* (2006.01)
*H01L 21/70* (2006.01)
*G01N 27/00* (2006.01)

(52) U.S. Cl.
CPC ......... *G01N 27/4145* (2013.01); *H01L 21/76* (2013.01); *H01L 29/772* (2013.01); *G01N 27/00* (2013.01); *H01L 21/70* (2013.01); *H01L 29/00* (2013.01)

(58) Field of Classification Search
None
See application file for complete search history.

(56) References Cited

U.S. PATENT DOCUMENTS

| 8,674,474 | B2 * | 3/2014 | Ackerson | H01L 29/772 257/522 |
|---|---|---|---|---|
| 2007/0235760 | A1 * | 10/2007 | Shim | H01L 29/78 257/192 |
| 2010/0175821 | A1 * | 7/2010 | Cho | B01L 3/502715 156/245 |
| 2011/0248320 | A1 * | 10/2011 | Rothberg | G01N 27/4145 257/253 |
| 2013/0105317 | A1 * | 5/2013 | Weber | B03C 5/005 204/451 |
| 2016/0077049 | A1 * | 3/2016 | Baghbani-Parizi | B82Y 15/00 438/49 |
| 2017/0234830 | A1 * | 8/2017 | White | G01N 27/4145 |

* cited by examiner

Primary Examiner — Asok K Sarkar
(74) Attorney, Agent, or Firm — Lin & Associates IP, Inc.

(57) ABSTRACT

The present invention provides a structure for integrating microfluidic devices and electrical biosensors, including: a substrate for carrying an electrical biosensor; a microfluidic channel layer for providing at least a fluid to flow; a cover member for the inflow and outflow of the at least a fluid, and an electrical biosensor, having a biosensing layer and mounted to the cover member in a flip-chip manner; wherein the fluid flows into an inlet, passes the electrical biosensor for sensing and flows out through a fluid outlet.

10 Claims, 2 Drawing Sheets

STRUCTURE FOR INTEGRATING MICROFLUIDIC DEVICES AND ELECTRICAL BIOSENSORS

CROSS-REFERENCE TO RELAYED APPLICATION

This application claims the priority of Taiwanese patent application No. 105126570, filed on Aug. 19, 2016, which is incorporated herewith by reference.

BACKGROUND

1. Field of the Invention

The technical field generally relates to a structure for integrating microfluidic devices and electrical biosensors.

2. The Prior Arts

With the continuous development of electronic technology, the applications expand into cross-discipline exploration and integration, wherein the emergence of biosensors is considered a major breakthrough in the rapid development of biological or medical technology. A biosensor is generally defined as analysis device using a biosensing device to translate the change of the chemical substance in the system into electronic signal or optical signal. The biosensor mainly comprises a sensor, a transducer and an electronic device.

Biosensors fulfill many of the important measurement needs. The most unique feature of biosensors is the high sensitivity, specificity, or selectivity of biosensors. The reason is that the organism itself has a variety of chemical receptors, in other words, the organism itself is actually a collection of chemoreceptors, and the chemoreceptors have a high degree of specificity or selectivity and sensitivity.

On the other hand, adding the mechanic components required in conventional biochemical analysis in a form of micro-pumps, micro-valves, micro-filters, micro-mixers, micro-channels, micro-sensors and micro-reactors to the microfluidic devices for sample pre-processing, mixing, transporting, separation and detection procedures has also be actively applied to the biosensor.

However, the known integrated structures of biosensors and microfluidic devices are often unable to provide quality uniformity, structural integrity, and process throughput for detection modules due to limitations of applications and existing integration manufacturing processes.

Moreover, the biosensing layer in the biosensor is often constrained by the bond formation of the chemical molecules and biomolecules with operation temperature below 100° C., sometimes even as low as 40° C. On the other hand, the attachment process of semiconductor elements and MEMS elements usually operates at a temperature higher than 100° C. At his temperature, the structure of the biomolecules and chemical molecules of the biosensing layer may be changed or lose natural activity, which renders the biosensing ineffective. Therefore, how to provide an effective and flexible structure for integrating microfluidic devices and electrical biosensors is an important industrial issue.

SUMMARY

An embodiment of the present invention discloses a structure for integrating microfluidic devices and electrical biosensors, comprising: a substrate, disposed with a plurality of first vias, wherein the plurality of first vias being filled with a conductive material, and a conductive pad being disposed at both ends of each of the plurality of first vias, the conductive pad being electrically connected to the conductive material inside the first vias; a flow channel layer, disposed on top of the substrate and comprising at least a channel for at least a fluid to flow, and a plurality of second vias, wherein the plurality of second vias being filled with a conductive material, and the conductive material being electrically connected to the conductive pad of the substrates; a cover member, disposed on top of the flow channel layer and having at least a fluid inlet and at least a fluid outlet for the inflow and outflow of the at least a fluid, wherein the at least a fluid inlet and the at least a fluid outlet being connected to the at least a channel of the flow channel layer, a window opening, wherein the window opening exposing the at least a fluid, and a plurality of third vias, wherein the plurality of third vias being filled with a conductive material and the conductive material being electrically connected to the conductive material inside the second vias of the flow channel layer; and an electrical biosensor, disposed and engaged to the cover element by flip chip bumps; wherein the electrical biosensor having a biosensing layer, and the window opening of the cover element contacting the biosensing layer when the at least a fluid flowing passing the window opening; the bumps being implanted inside the conductive material filling the plurality of third vias of the cover element to achieve electrical connection; wherein the at least a fluid flowing in from the at least a fluid inlet, through the at least a channel to the biosensing layer of the electrical biosensor thereon for sensing and out of the at least a fluid outlet.

The foregoing will become better understood from a careful reading of a detailed description provided herein below with appropriate reference to the accompanying drawings.

BRIEF DESCRIPTION OF THE DRAWINGS

The embodiments can be understood in more detail by reading the subsequent detailed description in conjunction with the examples and references made to the accompanying drawings, wherein.

DETAILED DESCRIPTION OF THE DISCLOSED EMBODIMENTS

Figure 1:
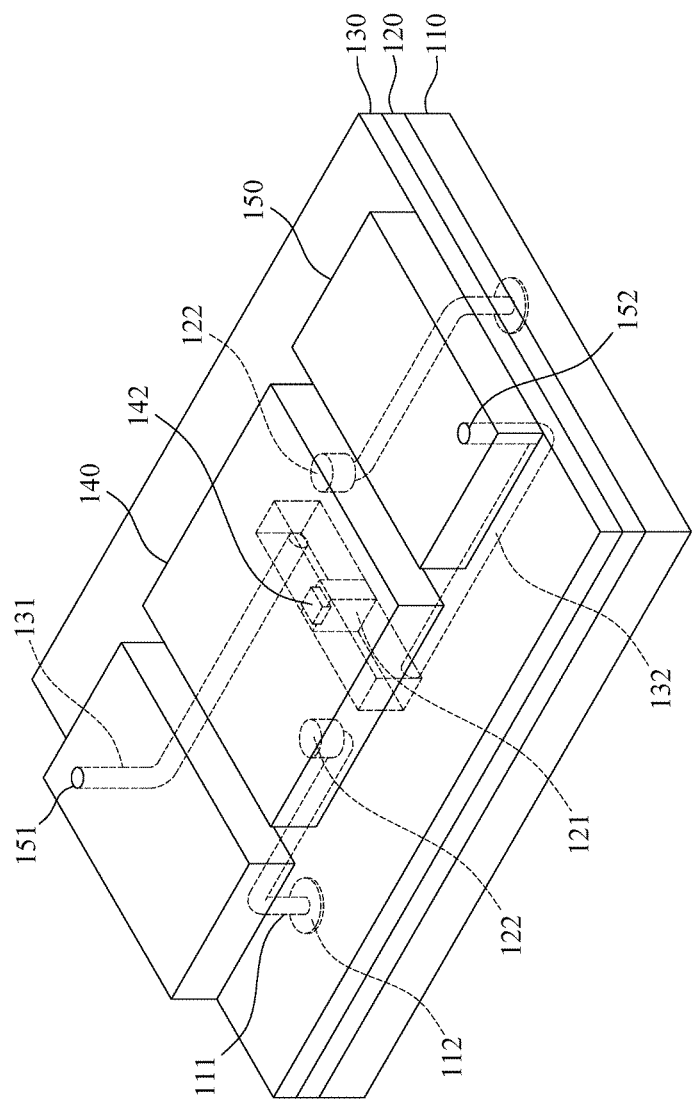
FIG. 1 shows a schematic view of a first embodiment of the structure for integrating microfluidic devices and electrical biosensors in accordance with an exemplary embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
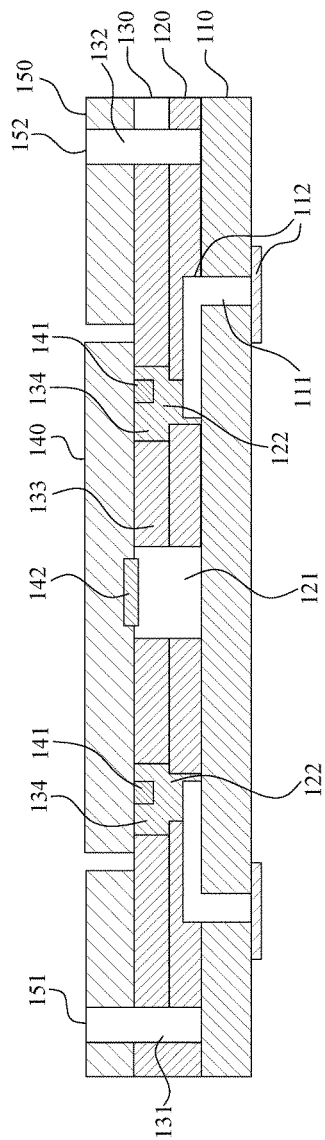
FIG. 2 shows cross-sectional view of the first embodiment of the structure for integrating microfluidic devices and electrical biosensors in accordance with an exemplary embodiment.

Refer to FIGS. 1-2. FIG. 1 shows a schematic view of the structure for integrating microfluidic devices and electrical biosensors in accordance with an exemplary embodiment; and FIG. 2 shows cross-sectional view of the structure for integrating microfluidic devices and electrical biosensors in accordance with an exemplary embodiment. The structure for integrating microfluidic devices and electrical biosensors is applied to form an integrated module comprising at least an electrical biosensor and at least a microfluidic device. As shown in FIGS. 1-2, the structure for integrating microfluidic devices and electrical biosensors comprises, from bottom up: structure for integrating microfluidic devices and electrical biosensors, comprising: a substrate 110, a flow channel layer 120, a cover element 130 and an electrical biosensor 140.

As shown in FIGS. 1 & 2, the substrate 110 is disposed with a plurality of first vias 111, wherein the plurality of first vias 111 being filled with a conductive material, and a conductive pad 112 is disposed at both ends of each of the plurality of first vias 111, the conductive pad 112 is electrically connected to the conductive material inside the first vias 111.

The flow channel layer 120 is disposed on top of the substrate 110 and comprises at least a channel 121 for at least a fluid to flow, and a plurality of second vias 122, wherein the plurality of second vias 122 is filled with a conductive material, and the conductive material is electrically connected to the conductive pad 112 of the substrates 110.

According to an embodiment of the present invention, the cover member 130 is disposed on top of the flow channel layer 120 and has at least a fluid inlet 131 and at least a fluid outlet 132 for the inflow and outflow of the at least a fluid, wherein the at least a fluid inlet 131 and the at least a fluid outlet 132 are connected to the at least a channel of the flow channel layer 120, wherein the at least a fluid flows in from the at least a fluid inlet 131, through the at least a channel to the biosensing layer 113 of the electrical biosensor 112 thereon for sensing and out of the at least a fluid outlet 132.

According to another embodiment of the present invention, the cover member 130 is disposed on top of the flow channel layer 120 and has at least a fluid inlet 131 and at least a fluid outlet 132 for the inflow and outflow of the at least a fluid, wherein the at least a fluid inlet 131 and the at least a fluid outlet 132 are connected to the at least a channel of the flow channel layer 120; a window opening 133, wherein the window opening 133 exposes the at least a fluid; and a plurality of third vias 134, wherein the plurality of third vias 134 is filled with a conductive material and the conductive material is electrically connected to the conductive material inside the second vias 122 of the flow channel layer 120.

The electrical biosensor 140 is disposed and engaged to the cover element 130 bumps 141 as a flip chip mounting; the bumps are implanted inside the conductive material filling the plurality of third vias 134 of the cover element 130 to achieve electrical connection. The electrical biosensor 140 further comprises a biosensing layer 142, and the window opening 133 of the cover element 130 contacts the biosensing layer 142 when the at least a fluid flows passing the window opening 133. Therefore, when the at least a fluid flows in from the at least a fluid inlet 131, through the at least a channel 121 to the window opening 133 of the cover element 130, the fluid contacts the biosensing layer 142 of the electrical biosensor 140 thereon for sensing and then flows out of the at least a fluid outlet 132.

Moreover, the substrate 110 can be further disposed with a circuit comprising active and passive elements; and the substrate 110 can be further designed as a stack structure comprising a multi-layer structure depending on the application to accommodate more complex circuit. Similarly, the flow channel 120 can further comprises a circuit, which is electrically connected to the circuit on the substrate 110, while the circuit and the connection junction are isolated from the at least a fluid. The cover element 130 can further comprises a circuit, which is electrically connected to the circuit on the flow channel layer 120, while the circuit and the connection junction are isolated from the at least a fluid.

In other words, the substrate 110, the flow channel layer 120, the cover element 130 and the electrical biosensor 140 can be disposed with a circuit respectively; and the substrate 110, the flow channel layer 120, the cover element 130 and the electrical biosensor 140 can all form electrical connection through the conductive pads 112, the first vias 111, the second vias 122, the third vias 134 and the bumps 141.

In a preferred embodiment of the present invention, the structure for integrating microfluidic devices and electrical biosensors further comprises a support protection plate 150, and the support protection plate 150 is disposed with a window opening to accommodate the electrical biosensor 140. The support protection plate 150 further comprises at least a second fluid inlet 151 and at least a second fluid outlet 152. The at least a second fluid inlet 151 and at least a second fluid outlet 152 is disposed correspondingly to the at least a fluid inlet 131 and the at least a fluid outlet 132 of the cover element 130.

It should be noted that in another preferred embodiment of the present invention, the substrate 110 is further disposed with at least a second fluid inlet and at least a second fluid outlet to provide flowing in and out for the at least a fluid. In such case, the support protection plate 150 will not be disposed with at least a second fluid inlet 151 or at least a second fluid outlet 152. Alternatively, the at least a second fluid inlet 151 is disposed at the support protection plate 150, and the at least a second fluid outlet 152 is disposed at the substrate 110, and vice versa. In other words, the at least a second fluid inlet 151 or at least a second fluid outlet 152 can be disposed either at the substrate 110 or the support protection plate 150 for the fluid to flow in and out from. In summary, the at least a fluid inlet, the at least a second fluid inlet, the at least a fluid outlet, and the at least a second fluid outlet must be disposed correspondingly to the channel 121 of the flow channel layer 120 to provide the fluid to flow in and out from, and the location of disposition can be changed depending on the application.

In a preferred embodiment of the present invention, the flow channel layer 120 may be made of a transparent or opaque material such as, polymeric material, plastic, ceramic, metal, silicon wafer, glass, or other composite material. The surface of the flow channel layer 120 may be processed to a hydrophilic or hydrophobic surface. The flow channel layer 120 may further comprise at least a pump element, at least a valve element, at least a mixer element, other microfluidic element, or any combination thereof for the flow and pretreatment of at least a fluid. Furthermore, the flow channel layer 120 may also be a multi-layer structure having a plurality of layers whose surfaces may be processed to show hydrophilic or hydrophobic characteristics.

In a preferred embodiment of the present invention, the cover member 130 may be made of a transparent material or an opaque material such as, polymeric material, plastic, ceramic, metal, silicon wafer, glass, or other composite material. Further, the flow channel layer 120 and the cover member 130 may be integrated into one piece, or the flow channel layer 120 and the substrate 110 may be integrated into an integrally formed structure to reduce the subsequent encapsulation or assembly process. It should also be noted other than the channel. The connection junction of all the components, such as, the substrate 110, the flow channel layer 102, and the cover element 130 must be isolated from the fluid to prevent leakage.

In a preferred embodiment of the present invention, the engagement between the electrical biosensor and the cover element is executed at a room temperature. Compared to the high-temperature process often used in semiconductor element or MEMS element, the engagement used in the present invention can avoid the damage to the biological and chemical properties of the biosensing layer of the electrical biosensor.

In summary, the structure for integrating microfluidic devices and electrical biosensors of the present invention is able to detect the electrical signal generated by the electrical biosensors. Moreover, the junctions between the components in the structure, with the exception of the channel, are able to isolate fluid to prevent fluid leakage. Hence, the structure of the present invention is applicable to various electrical biosensors and microfluidic devices.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A structure for integrating microfluidic devices and electrical biosensors, comprising:
    a substrate, disposed with a plurality of first vias, wherein the plurality of first vias being filled with a conductive material, and a conductive pad being disposed at both ends of each of the plurality of first vias, the conductive pad being electrically connected to the conductive material inside the first vias;
    a flow channel layer, disposed on top of the substrate and comprising at least a channel for at least a fluid to flow, and a plurality of second vias, wherein the plurality of second vias being filled with a conductive material, and the conductive material being electrically connected to the conductive pad of the substrates;
    a cover member, disposed on top of the flow channel layer and having at least a fluid inlet and at least a fluid outlet for the inflow and outflow of the at least a fluid, wherein the at least a fluid inlet and the at least a fluid outlet being connected to the at least a channel of the flow channel layer; a window opening, wherein the window opening exposing the at least a fluid; and a plurality of third vias, wherein the plurality of third vias being filled with a conductive material and the conductive material being electrically connected to the conductive material inside the second vias of the flow channel layer; and
    an electrical biosensor, disposed and engaged to the cover element by flip chip bumps; wherein the electrical biosensor having a biosensing layer, and the window opening of the cover element contacting the biosensing layer when the at least a fluid flowing passing the window opening; the bumps being implanted inside the conductive material filling the plurality of third vias of the cover element to achieve electrical connection;
    wherein the at least a fluid flowing in from the at least a fluid inlet, through the at least a channel to the biosensing layer of the electrical biosensor thereon for sensing and out of the at least a fluid outlet.

2. The structure for integrating microfluidic devices and electrical biosensors as claimed in claim 1, further comprising a support protection plate, wherein the support protection plate being disposed with a window opening to accommodate the electrical biosensor; the support protection plate further comprising at least a second fluid inlet and at least a second fluid outlet; the at least a second fluid inlet and at least a second fluid outlet being disposed correspondingly to the at least a fluid inlet and the at least a fluid outlet of the cover element.

3. The structure for integrating microfluidic devices and electrical biosensors as claimed in claim 1, further comprising a support protection plate, wherein the support protection plate being disposed with a window opening to accommodate the electrical biosensor; wherein the substrate being further disposed with at least a second fluid inlet and at least a second fluid outlet, and the at least a second fluid inlet and at least a second fluid outlet being disposed correspondingly to the two ends of the at least channel of the flow channel layer to provide the at least a fluid to flow in and out from.

4. The structure for integrating microfluidic devices and electrical biosensors as claimed in claim 1, wherein the substrate further comprises a circuit comprising active and passive elements.

5. The structure for integrating microfluidic devices and electrical biosensors as claimed in claim 1, wherein the substrate is a stack structure comprising a multi-layer substrate.

6. The structure for integrating microfluidic devices and electrical biosensors as claimed in claim 1, wherein the flow channel layer further comprises at least a pump element, at least a valve element, at least a mixer element, other microfluidic element, or any combination thereof for the flow and pretreatment of at least a fluid.

7. The structure for integrating microfluidic devices and electrical biosensors as claimed in claim 1, wherein the flow channel layer is a multi-layer structure.

8. The structure for integrating microfluidic devices and electrical biosensors as claimed in claim 1, wherein the flow channel layer further comprises a circuit, the circuit is electrically connected to the circuit of the substrate, and the circuit and the junction are isolated from the at least a fluid.

9. The structure for integrating microfluidic devices and electrical biosensors as claimed in claim 1, wherein the flow channel layer and the cover member are integrated into a monolithic element, or the flow channel layer and the substrate are integrated into a monolithic element.

10. The structure for integrating microfluidic devices and electrical biosensors as claimed in claim 1, wherein the cover element further comprises a circuit, the circuit is electrically connected to the circuit of the flow channel layer, and the circuit and the junction are isolated from the at least a fluid.

* * * * *